United States Patent [19]  [11] 4,079,054
Green et al.                                [45] Mar. 14, 1978

[54] 7α-HALOGENO-3-OXO-1,4-PREGNADIENE-21,17β-CARBOLACTONES AND RELATED COMPOUNDS

[75] Inventors: Michael J. Green, Kendall Park; Ho-Jane Shue, Belleville, both of N.J.

[73] Assignee: Schering Corporation, Kenilworth, N.J.

[21] Appl. No.: 753,258

[22] Filed: Dec. 22, 1976

[51] Int. Cl.$^2$ ............................ C07J 21/00; C07J 1/00
[52] U.S. Cl. ...................... 260/239.57; 260/239.55 R; 260/397.3; 260/397.4
[58] Field of Search ...................... 260/239.55, 239.57; /Machine Searched Steroids

[56] References Cited
U.S. PATENT DOCUMENTS 3,509,136   4/1970   Brown ............................ 260/239.57
3,845,041  10/1974   Chinn ............................ 260/239.57

Primary Examiner—Elbert L. Roberts
Attorney, Agent, or Firm—Mary S. King; Stephen B. Coan

[57] ABSTRACT

Described are 3-oxo-7α-halogeno-17α-1,4-pregnadiene-21,17β-carbolactones and compounds related thereto, i.e. 2′,3′α-tetrahydrofuran-2′-spiro-17(7α-halogeno-1,4-androstadiene-3-ones) and (17R)-spiro-[7α-halogeno-1,4-androstadiene-17,1′-cyclobutane]-3,2′-diones, all of which are valuable as aldosterone antagonists. Also described are the corresponding 7β-hydroxy derivatives useful as intermediates.

8 Claims, No Drawings

7α-HALOGENO-3-OXO-1,4-PREGNADIENE-21,17β-CARBOLACTONES AND RELATED COMPOUNDS

FIELD OF INVENTION

This invention relates to novel steroidal compositions-of-matter, to methods for their manufacture and to intermediates useful therein.

More specifically, this invention is concerned with 3-oxo-7α-halogeno-17α-1,4-pregnadiene-21,17β-carbolactones, and related compounds, i.e. 2',3'α-tetrahydrofuran-2'-spiro-17(7α-halogeno-1,4-androstadiene-3-ones) and (17R)-spiro-[7α-halogeno-1,4-androstadiene-17,1'-cyclobutane]-3,2'-diones, useful as aldosterone antagonists, to methods for their manufacture, and to intermediates useful therein.

PRIOR ART

Known in the art are 3-oxo-17α-1,4-pregnadiene-21,17β-carbolactone, 2',3'α-tetrahydrofuran-2'-spiro-17(1,4-androstadiene-3-one), (17R)-spiro-[1,4-androstadiene-17,1'-cyclobutane]-3,2'-dione, and 7-substituted derivatives thereof, e.g. 7α-thioacetyloxy and 6,7-methylene derivatives of 3-oxo-17α-1,4-pregnadiene-21,17β-carbolactone and of 2',3'α-tetrahydrofuran-2'-spiro-17(1,4-androstadiene-3-one), useful as aldosterone antagonists.

By our invention, novel 7α-halogeno derivatives of the foregoing 7-unsubstituted compounds have been prepared and found to possess anti-aldosterone activity.

DESCRIPTION OF THE COMPOSITION-OF-MATTER ASPECT OF THE INVENTION

The composition-of-matter aspect of this invention resides in the concept of 7α-halogeno derivatives of 3-oxo-17α-1,4-pregnadiene-21,17β-carbolactone, 2',3'α-tetrahydrofuran-2'-spiro-17(1,4-androstadiene-3-one) and of (17R)-spiro-[1,4-androstadiene-17,1'-cyclobutane]-3,2'-dione, preferably 7α-chloro and 7α-bromo derivatives, having anti-aldosterone activity.

Thus, included within our invention are 7α-halogeno derivatives of following formulae I and II:

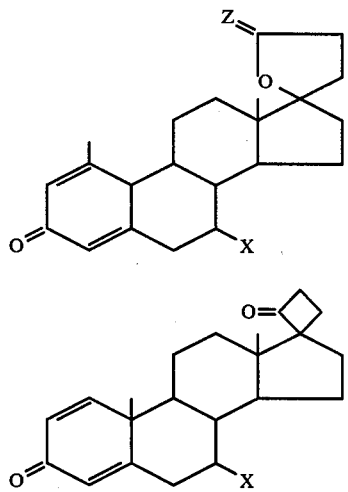

wherein X is halogen and Z is oxygen or hydrogen.

The halogens at C-7 as defined by X include fluorine, chlorine, bromine and iodine. Of the foregoing derivatives, preferred are the 7α-bromo and 7α-chloro derivatives.

Our invention thus includes: 7α-halogeno derivatives of formula I wherein Z is oxygen, i.e.

3-oxo-7α-fluoro-17α-1,4-pregnadiene-21,17β-carbolactone,
3-oxo-7α-chloro-17β-1,4-pregnadiene-21,17β-carbolactone,
3-oxo-7α-bromo-17α-1,4-pregnadiene-21,17β-carbolactone, and
3-oxo-7α-iodo-17β-1,4-pregnadiene-21,17β-carbolactone;

7α-halogen derivatives of formula I wherein Z is hydrogen, i.e.

2',3'α-tetrahydrofuran-2'-spiro-17(7α-fluoro-1,4-androstadiene-3-one),
2',3'α-tetrahydrofuran-2'-spiro-17(7α-chloro-1,4-androstadiene-3-one),
2',3'α-tetrahydrofuran-2'-spiro-17(7α-bromo-1,4-androstadiene-3-one), and
2',3'α-tetrahydrofuran-2'-spiro-17(7α-iodo-1,4-androstadiene-3-one);

7α-halogen derivatives of formula II, i.e.
(17R)-spiro-[7α-fluoro-1,4-androstadiene-17,1'-cyclobutane]-3,2'-dione,
(17R)-spiro-[7α-chloro-1,4-androstadiene-17,1'-cyclobutane]-3,2'-dione,
(17R)-spiro-[7α-bromo-1,4-androstadiene-17,1'-cyclobutane]-3,2'-dione,
(17R)-spiro-[7α-iodo-1,4-andostradiene-17,1'-cyclobutane]-3,2'-dione.

Of the foregoing, preferred are the 7α-halogen pregnadiene-21,17β-carbolactones of formula I wherein Z is oxygen, particularly the 7α-chloro and 7α-bromo derivatives.

The 7α-halogen compounds of formulae I and II exhibit aldosterone antagonist activity and, as such, are useful in the treatment of primary aldosteronism and as diuretic agents especially in the treatment of hepatic cirrhosis and in nephrotic syndrome. Also, they are useful in treating various types of hypertension and in congestive heart failure. The aldosterone antagonists are usually administered orally or parenterally in effective doses dependent upon the nature and severity of the ailment and on the age and weight of the patient.

In addition to exhibiting aldosterone antagonist activity per se, 3-oxo-7α-halogeno-1,4-androstadiene-17-spirobutanones of formula II are useful as intermediates since, upon treatment with a Bayer-Villager oxidation reagent, e.g. with alkaline hydrogen peroxide, (17R)-spiro-[7α-halogeno-1,4-androstadiene-17,1'-cyclobutane]-3,2'-diones of formula II, e.g. the 7α-fluoro and 7α-chloro derivatives thereof, are converted to the corresponding 3-oxo-7α-halogeno-17α-1,4-pregnadiene-21,17β-carbolactones of formula II (i.e. compounds wherein Z is oxygen), i.e. 3-oxo-7α-fluoro-17α-1,4-pregnadiene-21,17β-carbolactone and 3-oxo-7α-chloro-17α-1,4-pregnadiene-21,17β-carbolactone.

Additionally, the 2',3'α-tetrahydrofuran-2'-spiro-17-(7α-halogen-1,4-androstadiene-3-ones) of formula I (i.e. wherein Z is hydrogen) in addition to being anti-aldosterone agents, are also useful as intermediates in the preparation of the preferred compounds of formula I wherein Z is oxygen. Thus, a 7α-halogen compound of formula I wherein Z is hydrogen (e.g. 2',3'α-tetrahydrofuran-2'-spiro-17(7α-fluoro-1,4-androstadiene- 3-one), in chloroform solution, upon reaction with an oxidizing reagent such as tert.-butyl chromate (prepared by reaction of chromium trioxide with tert.-butanol at room temperature) in anhydrous carbon tetrachloride containing acetic ahydride and acetic acid at reflux temperature, followed by treatment with a reducing agent such as aqueous oxalic acid, thence isolation of the oxidized product utilizing techniques known in the art (e.g. extraction techniques) and purification (usually via chromatographic techniques) yields a 21,17β-carbolactone of formula I wherein Z is oxygen, e.g. 3-oxo-7α-1,4-pregnadiene-21,17β-carbolactone.

Another composition-of-matter aspect of this invention resides in the concept of 7β-hydroxy derivatives of 7-unsubstituted analogs of formulae I and II, useful intermediates in preparing the 7α-halogeno aldosterone antagonists of this invention, as described in greater detail hereinbelow, which also possess anti-aldosterone activity. These intermediates include: 3-oxo-7β-hydroxy-17α-1,4-pregnadiene-21,17β-carbolactone, 2',3'α-tetrahydrofuran-2'-spiro-17(7β-hydroxy-1,4-androstadien-3-one) and (17R)-spiro-[7β-hydroxy-1,4-androstadiene-17,1'-cyclobutane]-3,2'-dione.

PROCESS ASPECTS OF THE INVENTION

The 7α-chloro-, 7α-bromo- and 7α-iodo- derivatives of formulae I and II are conveniently prepared by reaction of the corresponding hydrogen halide with a 7-unsubstituted-6-dehydroanalog of formula I and II in a non-reactive, organic solvent.

The process is preferably carried out under anhydrous conditions, saturated solutions of hydrogen halide in solvent being preferably employed to minimize reaction time.

Solvents suitable for use in this process include any non-reactive organic solvent in which the starting 7-unsubstituted 3-oxo-1,4,6-triene compound and the hydrogen halide are soluble. By "non-reactive" is meant any organic solvent which will not react with the steroid substrate or the hydrogen halide which would cause transformations resulting in competing side reactions.

Particularly useful solvents for our hydrogen halide addition process are ethers such as dioxane, tetrahydrofuran and diethylether; chlorinated solvents such as chloroform, methylene chloride and 1,2-ethylenedichloride; organic acids such as acetic and propionic acids; tertiary amides such as dimethylformamide, diethylformamide, and hexamethylphosphortriamide; dimethylsulfoxide; and hydrocarbons such as hexane and benzene.

When carrying out our process we usually use dioxane, acetic acid or tetrahydrofuran as solvent, tetrahydrofuran being preferred for reactions with hydrogen chloride and acetic acid for reactions with hydrogen bromide or hydrogen iodide.

Our reaction whereby a hydrogen halide is added to a 6-dehydro bond is preferably carried out at temperatures in the range of from about 0° C to about room temperature (e.g. 20° C) although lower temperatures (e.g. −20° C) and temperatures as high as about 60° C may be employed. The reaction time depends upon the hydrogen halide, solvent, and concentration being employed. Thus for example, the addition of hydrogen iodide in acetic acid is usually complete within one or two minutes; while the addition reaction utilizing hydrogen bromide in acetic acid at room temperature may be completed in from 20 to 60 minutes.

Generally, when carrying out this process whereby a hydrogen halide is added to a 6-dehydro bond, to a saturated solution of dry hydrogen halide in an anhydrous solvent (e.g. hydrogen bromide in acetic acid) usually at 0° C to 20° C, is added the starting 3-oxo-1,4,6-triene (e.g. 3-oxo-17α-1,4,6-pregnatriene-21,17β-carbolactone) either in the solid state or in solution, the molar quantity of hydrogen halide to steroid being about 40 to 1. After the reaction is complete, as determined by thin layer chromatography, the reaction mixture is poured into ice water and the resultant precipitate of 7α-halogeno-3-oxo-1,4-diene (e.g. 3-oxo-7α-chloro-17α-1,4-pregnadiene-21,17β-carbolactone) is isolated via filtration or extraction techniques and purified utilizing known techniques usually via chromatography.

The 3-oxo-1,4,6-triene starting compounds of the foregoing process are either known compounds or are conveniently prepared from the corresponding 3-oxo-4,6-diene utilizing techniques known to effect dehydrohalogenation between C-1 and C-2 such as those utilizing 2,3-dichloro-5,6-dicanobenzoquinone (DDQ) in refluxing benzene-dioxane.

The 7α-fluoro compounds of our invention are conveniently prepared by reaction of the corresponding 7β-hydroxy derivative with N-(2-chloro-1,1,2-trifluoroethyl)diethylamine (also known as fluoramine) in a halogenated solvent, preferably methylene chloride.

This process is preferably carried out at about 0° C under an inert atmosphere (e.g. argon, neon, nitrogen) under anhydrous conditions.

In a preferred mode of preparing a 7α-fluoropregnadiene of our invention (e.g. 3-oxo-7α-fluoro-17α-1,4-pregnadiene-21,17β-carbolactone) there is added fluoramine to an anhydrous solution of a 7β-hydroxy-3-oxo-1,4-diene (e.g. 3-oxo-7β-hydroxy-17α-1,4-pregnadiene-21,17β-carbolactone) in a halogenated solvent (usually methylene chloride), at about 0° C, the molar quantity of fluoramine to steroid being 6 to 1. The reaction is continued until completed as determined by thin layer chromatography and the product isolated by evaporation of the reaction mixture and purified via chromatographic techniques to obtain the desired 7α-fluoro derivative (e.g. 3-oxo-7α-fluoro17α-1,4-pregnadiene-21,17β-carbolactone), sometimes in admixture with the corresponding 7-unsubstituted-6-dehydro derivative (e.g. 3-oxo-16α-1,4,6-pregnatriene-21,17β-carbolactone thereof). Separation of such a mixture may be effected by separating the mixture of 3-oxo-7α-fluoro-17α-1,4-pregnadiene and 3-oxo-17α-1,4,6-pregnatriene via chromatographic techniques.

The 3-oxo-7β-hydrox-1,4-diene precursors in the foregoing process are also useful intermediates in processes for preparing 7α-chloro- and 7α-bromo-1,4-dienes of formulae I and II Thus, 3-oxo-7α-chloro-17α-1,4-pregnadiene (e.g. 3-oxo-7α-chloro-17α-1,4-pregnadiene-21,17β-carbolactone) are prepared from the corresponding 7α-hydroxy derivative by reaction thereof in a halogenated solvent (preferably methylene chloride) at about 0° C under an inert atmosphere (e.g. nitrogen) with N,N-diethyl-1,2,2-trichlorovinylamine, the molar quantity of reagent to steroid usually being in the range of 6 to 1.

Additively, 7α-chloro-3-oxo-1,4-dienes of formulae I and II are prepared from the corresponding 7β-hydroxy derivative by reaction thereof with lithium chloride and fluoramine in a halogenated solvent (e.g. methylene chloride) at about 0° C, the molar quantity of lithium chloride and fluoramine per mole of starting 7β-hydroxy-3-oxo-1,4-diene being 12 and 6, respectively.

Similarly, to prepare 7α-bromo-1,4-dienes of formulae I and II (e.g. 3-oxo-7α-bromo-17α-1,4-pregnadiene-21,17β-carbolactone 21-acetate), the corresponding 7β-hydroxy derivative is reacted with fluoramine and lithium bromide at about 0° C in a halogenated solvent (usually methylene chloride), the molar quantities of lithium bromide and fluoramine per mole of steroid being 12 and 6, respectively.

The 7β-hydroxy-3-oxo-1,4-diene intermediates for the foregoing processes are novel compounds which are prepared by conversion of the corresponding 6β,7β-dihydroxy derivatives to a 6β,7β-alkylorthoalkanoate ester, followed by cleavage thereof with acid utilizing known techniques, thence reaction of the thereby formed 6β-acyloxy-7β-hydroxy derivatives with chromous acetate and sodium acetate in aqueous acetic acid. Thus, for example, 3-oxo-7β-hydroxy-1,4-pregnadiene-21,17β-carbolactone is prepared by reaction of the corresponding 6β,7β-dihydroxy derivatives with tri-n-butylorthopropionate and p-toluenesulfonic acid monohydrate in dimethylsulfoxide followed by cleavage of the 3-oxo-6β,7β-n-butylorthopropionyloxy-21,17β-carbolactone thereby formed with aqueous acetic acid and thence reaction of the resulting 6β-propionyloxy-7β-hydroxy derivative with chromous acetate and sodium acetate to give a 7β-hydroxy intermediate of this invention, 3-oxo-7β-hydroxy-17α-1,4-pregnadiene-21,17βcarbolactone.

The molecular structure of the compounds of the invention were assigned on the basis of their method of preparation, and a study of their chromatographic characteristics and their nuclear magnetic resonance (nmr), mass and ultraviolet spectra, and were confirmed by the correspondence between calculated and found values of elemental analyses for the elements.

The processes described hereinabove are illustrated in detail in the Examples hereinbelow and should not be construed as limiting the scope of the invention, equivalents thereof and products produced thereby, which will be obvious to one skilled in the art, being considered a part of the invention.

EXAMPLE 1

3-OXO-7α-CHLORO-17α-1,4-PREGNADIENE-21,17β-CARBOLACTONE

A. 3-Oxo-17α-1,4,6-Pregnatriene-21,17β-Carbolactone

To a solution of 3-oxo-17α-4,6-pregnadiene-21,17β-carbolactone (20 gms.) in benzene (600 ml.) and dioxane (600 ml.) add 2,3-dichloro-5,6-dicyanobenzoquinone (DDQ) (80 gms.) and stir the reaction mixture at reflux temperature for 18 hours. Cool the reaction mixture, filter, and evaporate the filtrate in vacuo. Dissolve the resultant residue in a minimum amount of chloroform and place on a column containing 200 gms. of alumina and elute with chloroform (1 liter). Evaporate the eluate in vacuo to a residue comprising 3-oxo-17α-1,4,6-pregnatriene-21,17β-carbolactone. Purify by crystallization from acetone:ethyl ether.

B.
3-Oxo-7α-Chloro-17α-1,4-Pregnadiene-21,17β-Carbolactone (1) To dry tetrahydrofuran (40 ml.) previously saturated with dry hydrogen chloride gas at 0°-5° C, add 3-oxo-17α-1,4,6-pregnatriene-21,17β-carbolactone (2 gms.) and stir at 0°–5° C for 1 hour. Pour the reaction mixture into ice water (400 ml.) and separate the resultant precipitate by filtration, wash the precipitate with water and dry to obtain 3-oxo-7α-chloro-17α-1,4-pregnadiene-21,17β-carbolactone. Purify by crystallization from acetone:hexane $[\alpha]_D^{26}$ + 6.8° (dimethylformamide); $\lambda_{max}^{methanol}$ 243 mμ (ε15,920); m.p. 133°–136° C.

(2) In similar manner, treat each of (17R)-spiro-[1,4,6-androstatriene-17,1'-cyclobutane]-3,2'-dione and 2',3'α-tetrahydrofuran-2'-spiro-17(1,4,6-androstatriene-3-one) with dry hydrogen chloride in tetrahydrofuran at 0.5° C and isolate each of the resultant products in a manner similar to that described to obtain, respectively, (17R)-spiro-[7α-chloro-1,4-androstadiene-17,1'-cyclobutane]-3,2'-dione and 2',3'α-tetrahydrofuran-2'-spiro-17(7α-chloro-1,4-androstadiene-3-one).

EXAMPLE 2

3OXO-7α-BROMO-17α-1,4-PREGNADIENE-21,17β-CARBOLACTONE (1) Bubble dry hydrogen bromide (7.5 gms.) into glacial acetic acid (12.5 ml.) at 5°–10° C. Then add a solution of 3-oxo-17α-1,4,6-pregnatriene-21,17β-carbolactone (1 gm.) in glacial acetic acid. Stir the reaction mixture at 5° C for 45 minutes, then pour into ice water (250 ml.) and separate the resultant precipitate by filtration, wash with water and dry to obtain 3-oxo-7α-bromo-17α-1,4-pregnadiene-21,17β-carbolactone. Purify by crystallization from acetone/hexane/ether; $[\alpha]_D^{26}$ + 7.7° (dimethylformamide); $\lambda_{max}^{methanol}$ 243 mμ (ε15,100); m.p. 125°–130° C (dec.).

(2) In similar manner, treat each of (17R)-spiro-[1,4,6-androstatriene-17,1'-cyclobutane]-3,2'-dione and 2',3'α-tetrahydrofuran-2'-spiro-17(1,4,6-androstatriene-3-one) with dry hydrogen bromide in glacial acetic acid and isolate each of the resultant products in similar manner to obtain, respectively, (17R)-spiro-[7α-bromo-1,4-androstadiene-17,1'-cyclobutane]-3,2'-dione and 2',3'α-tetrahydrofuran-2'-spiro-17(7α-bromo-1,4-androstadiene-3-one).

EXAMPLE 3

3-OXO-7α-IODO-17α-1,4-PREGNADIENE-21,17β-CARBOLACTONE (1) Bubble hydrogen iodide (2.6 gms.) into glacial acetic acid (10 ml.) at 5°–10° C, then add 3-oxo-17α-1,4,6-pregnatriene-21,17β-carbolactone (0.5 gms.) and stir at 5°–10° C for 45 minutes. Pour the reaction mixture into ice water (150 ml.) containing sodium thiosulfatepentahydrate (5 gms.) Separate the resultant precipitate by filtration, wash the precipitate with water and dry in vacuo to obtain 3-oxo-7α-iodo-17α-1,4-pregnadiene-21,17β-carbolactone. Purify by dissolving in a minimum amount of ethyl acetate and separating the components in the foregoing precipitate on silica gel via thin layer chromatography utilizing as developing solvent chloroform:ethyl acetate (1:1) and eluting with a solvent mixture of 15% acetone in ethyl acetate the band containing the desired product as shown by ultraviolet light. Evaporate the combined eluates to a residue comprising 3-oxo-7α-iodo-17α-1,4-pregnadiene-21,17β-carbolactone.

(2) In similar manner, treat each of (17R)-spiro-[1,4,6-androstatriene-17,1'-cyclobutane]-3,2'-dione and 2',3'α-tetrahydrofuran-2'-spiro-17(1,4,6-androstatriene-3-one) with dry hydrogen iodide in glacial acetic acid and isolate and purify each of the resultant products in the manner similar to that described to obtain, respectively, (17R)-spiro-[7α-iodo-1,4-androstadiene-17,1'-cyclobutane]-3,2'-dione and 2',3'α-tetrahydrofuran-2'-spiro-17(7α-iodo-1,4-androstadiene-3-one).

EXAMPLE 4

3-OXO-7α-FLUORO-17α-1,4-PREGNADIENE-21,17β-CARBOLACTONE

A.

3-Oxo-6β,7β-Dihydroxy-17α-1,4-Pregnadiene-21,17β-Carbolactone

To 3-oxo-17α-1,4,6-pregnatriene-21,17β-carbolactone (3.38 gms.; 0.01 mol) in dioxane (60 ml.) containing pyridine (8 ml.) add osmium tetroxide (2.627 gms.) dissolved in dioxane (100 ml.). Stir the reaction mixture at room temperature for 8 days, then bubble hydrogen sulfide vigorously through the reaction mixture. Continue stirring the reaction mixture at room temperature for 3 hours, then filter through supercel and evaporate the filtrate in vacuo. Dissolve the resultant residue in a minimum amount of chloroform and place on a column of silica gel (200 gms.) and elute with ethyl acetate:chloroform (4:1). Combine the like eluates containing the desired compound as determined by thin layer chromatography and evaporate the combined eluates to a residue comprising 3-oxo-6β,7β-dihydroxy-17α-1,4-pregnadiene-21,17β-carbolactone. Purify by crystallization from acetone: hexane; m.p. 236°–240° C.

B.

3-Oxo-6β,7β-Dihydroxy-17α-1,4-Pregnadiene-21,17β-Carbolactone 6,7-n-Butylorthopropionate To 3-oxo-6β,7β-dihydroxy-17α-1,4-pregnadiene-21,17β-carbolactone (3 gms.) in dimethylsulfoxide (15 ml.) add tri-n-butylorthopropionate (5.4 ml.) and p-toluenesulfonic acid monohydrate (0.225 gms.) and stir at room temperature for 3.5 hours. Pour the reaction mixture into water (500 ml.) and saturated aqueous sodium bicarbonate (100 ml.). Extract the aqueous mixture with ethyl acetate, wash the combined extracts with water, dry over magnesium sulfate and evaporate to a residue comprising 3-oxo-6β,7β-dihydroxy-17α-1,4-pregnadiene-21,17β-carbolactone-6,7-n-butylorthopropionate.

C.

3-Oxo-6β,7β-Dihydroxy-17α-1,4-Pregnadiene-21,17β-Carbolactone 6-Propionate

Dissolve the products of Example 4B in glacial acetic acid (50 ml.) and water (1 ml.). Allow the reaction mixture to stand at room temperature for 1 hour, then pour into ice water (500 ml.) and separate the resultant precipitate by filtration. Wash the resultant precipitate with water to obtain 3-oxo-6β,7β-dihydroxy-17α-1,4-pregnadiene-21,17β-carbolactone 6-propionate.

D.

3-Oxo-7β-Hydroxy-17α-1,4-Pregnadiene-21,17β-Carbolactone

To 3-oxo-6β,7β-dihydroxy-17α-1,4-pregnadiene-21,17β-carbolactone 6-propionate (3 gms.) in acetone (750 ml.) add a solution of sodium acetate (21 gms.), water (60 ml.) and acetic acid (15 ml.) followed by chromous acetate sludge (freshly prepared from 70 gms. of chromic chloride reduced by zinc amalgam followed by treatment with sodium acetate (known method). Stir the reaction mixture at room temperature for 2½ hours and filter and evaporate. Add water to the resultant residue, extract with ethyl acetate, wash the combined organic extracts with water, dry and evaporate in vacuo to a residue comprising 3-oxo-7β-hydroxy-17α-1,4-pregnadiene-21,17β-carbolactone.

E.

3-Oxo-7α-Fluoro-17α-1,4-Pregnadiene-21,17β-Carbolactone

To 3-oxo-7β-hydroxy-17α-1,4-pregnadiene-21,17β-carbolactone (0.13 gms.) in methylene chloride (15 ml.) at 0° C under an atmosphere of nitrogen, add N-(2-chloro-1,1,2-trifluoroethyl)diethylamine (fluoramine) (0.286 ml.). Stir at 0° C for 18 hours, then evaporate in vacuo and purify the resultant residue via thin layer chromatography developing with chloroform:ethyl acetate (5:2) to obtain 3-oxo-7α-fluoro-17α-1,4-pregnadiene-21,17β-carbolactone.

F. Subject each of (17R)-spiro-[1,4,6-androstatriene-17,1'-cyclobutane]-3,2'-dione and 2',3'α-tetrahydrofuran-2'-spiro-17(1,4,6-androstatriene-3-one) to the series of reactions described in Examples 4A-4E to obtain, respectively, (17R)-spiro[7α-fluoro-1,4-androstadiene-17,1'-cyclobutane]-3,2'-dione and 2',3'α-tetrahydrofuran-2'-spiro-17(7α-fluoro-1,4-androstadiene-3-one).

EXAMPLE 5

ALTERNATE PROCEDURE FOR PREPARING 7α-CHLORO DERIVATIVES

A. To 3-oxo-7β-hydroxy-17α-1,4-pregnadiene-21,17β-carbolactone (0.5 gms.) in methylene chloride (100 ml.) at 0° C under an atmosphere of nitrogen add N,N-diethyl-1,2,2-trichlorovinylamine (1.67 ml.). Stir at 0° C for 7 hours, evaporate in vacuo, place the resultant residue on a silica gel column (50 gms.) and elute with chloroform:ethyl acetate (3:1). Combine like fractions containing the desired compound as determined by thin layer chromatography and evaporate. Further purify the resultant residue on thin layer silica gel plates developing with chloroform:ethyl acetate (3:1). Remove the band containing the desired product as visualized under ultraviolet light and elute with ethyl acetate. Evaporate the combined eluates to a residue comprising 3-oxo-7α-chloro-17α-1,4-pregnadiene-21,17β-carbolactone.

B. To a solution of 3-oxo-7β-hydroxy-17α-1,4-pregnadiene-21,17β-carbolactone (0.5 gms.) and lithium chloride (0.5 gms.) in tetrahydrofuran (250 ml.) cooled to 0° C, add fluoramine (1.18 ml.). Stir at 0° C for 24 hours, then evaporate in vacuo. Dissolve the resultant residue in chloroform, wash the chloroform solution with water, dry over magnesium sulfate and evaporate. Purify via thin layer chromatography utilizing as developing solvent chloroform: ethyl acetate (2:1). Remove the band containing the desired product as visualized under ultraviolet light and elute with ethyl acetate. Evaporate the combined ethyl acetate eluates in vacuo to a residue comprising 3-oxo-7α-chloro-17α-1,4-pregnadiene-21,17β-carbolactone.

C. Treat each of (17R)-spiro-[7β-hydroxy-1,4-androstadiene-17,1'-cyclobutane]-3,2'-dione and 2',3'α-tetrahydrofuran-2'-spiro-17(7β-hydroxy-1,4-androstadiene-3-one) in a manner similar to that described in either above Procedure 5A or Procedure 5B to obtain the corresponding 7α-chloro derivative, i.e. (17R)-spiro-[7α-chloro-1,4-androstadiene-17,1'-cyclobutane]-3,2'-dione and 2',3'α-tetrahydrofuran-2'-spiro-17(7α-chloro-1,4-androstadiene-3-one).

EXAMPLE 6

ALTERNATE PROCEDURE FOR PREPARING 7α-BROMO DERIVATIVES (1) In the procedure of Example 5B, by substituting for lithium chloride an equivalent quantity of lithium bromide and by utilizing methylene chloride as solvent instead of tetrahydrofuran, there is obtained the corresponding 7α-bromo compound, i.e. 3-oxo-7α-bromo-17α-1,4-pregnadiene-21,17β-carbolactone.

(2) Similarly, by treating each of the 7β-hydroxy starting compounds of Example 5C with fluoramine and lithium bromide in tetrahydrofuran, there is obtained the corresponding 7α-bromo derivative, i.e. (17R)-spiro-[7α-bromo-1,4-androstadiene-17,1'-cyclobutane]-3,2'-dione and 2',3'α-tetrahydrofuran-2'-spiro-17(7α-bromo-1,4-androstadiene-3-one).

EXAMPLE 7

ALTERNATE PROCEDURE FOR MAKING THE 7α-FLUORO AND 7α-CHLORO DERIVATIVES OF THE 3-OXO-17α-1,4-PREGNADIENE-21,17β-CARBOLACTONE (1) To 30% hydrogen peroxide (0.0048 ml.) and 9 N sodium hydroxide (0.0068 ml.) in methanol (0.5 ml.) add (17R)-spiro-[7α-fluoro-1,4-androstadiene-17,1'-cyclobutane]-3,2'-dione (22 mg.) and stir the reaction mixture at room temperature under an atmosphere of nitrogen for 1 hour. Add water to the reaction mixture and then add 1 N hydrochloric acid until the solution is at a pH of about 7. Extract the reaction mixture with ethyl acetate, wash the ethyl acetate extracts with water, dry over magnesium sulfate and evaporate to a residue comprising 3-oxo-7α-fluoro-17α-1,4-pregnadiene-21,17β-carbolactone. Purify via thin layer chromatography developing with chloroform:ethyl acetate (4:1). and eluting with chloroform:ethyl acetate the band containing the desired product as visualized under ultraviolet light. Evaporate the chloroform:ethyl acetate solution to a residue comprising 3-oxo-7α-1,4-pregnadiene-21,17β-carbolactone.

(2) In similar manner, in the above procedure by starting with (17R)-spiro-[7α-chloro-1,4-androstadiene-17,1'-cyclobutane]-3,2'-dione, there is obtained 3-oxo-7α-chloro-17α-1,4-pregnadiene-21,17β-carbolactone.

We claim:

1. A compound of following formulae I and II

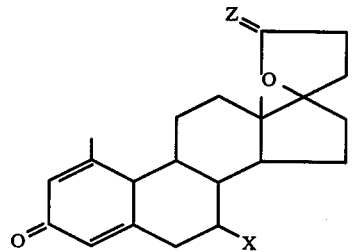

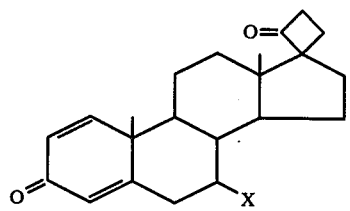

wherein X is halogen and Z is oxygen or hydrogen.

2. A compound of claim 1 wherein X is chlorine or bromine.

3. A compound of claim 1, formula I, wherein Z is oxygen.

4. A compound of claim 3 which is 3-oxo-7α-chloro-17α-1,4-pregnadiene-21,17β-carbolactone.

5. A compound of claim 3 which is 3-oxo-7α-bromo-17α-1,4-pregnadiene-21,17β-carbolactone.

6. A compound of claim 3 which is 3-oxo-7α-iodo-17α-1,4-pregnadiene-21,17β-carbolactone.

7. A compound of claim 3 which is 3-oxo-7α-fluoro-17α-1,4-pregnadiene-21,17β-carbolactone.

8. A compound selected from the group consisting of 3-oxo-7β-hydroxy-17α-1,4-pregnadiene-21,17β-carbolactone, 2',3'α-tetrahydrofuran-2'-spiro-17(7β-hydroxy-1,4-androstadiene-3-one) and (17R)-spiro-[7β-hydroxy-1,4-androstadiene-17,1'-cyclobutane]-3,2'-dione.

* * * * *

UNITED STATES PATENT OFFICE
CERTIFICATE OF CORRECTION

Patent No. 4,079,054                    Dated March 14, 1978

Inventor(s) Michael J. Green et al

It is certified that error appears in the above-identified patent and that said Letters Patent are hereby corrected as shown below:

Column 1, lines 47-64, Formulae I and II, and claim 1, column 10, lines 6-24, Formulae I and II, " 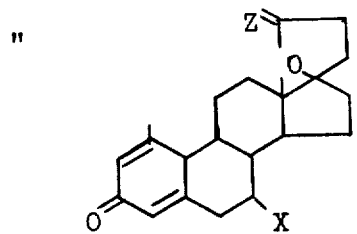   I        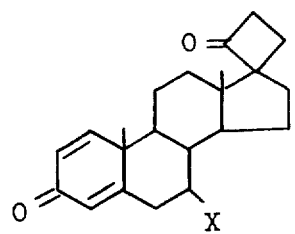   II "

should read

--- 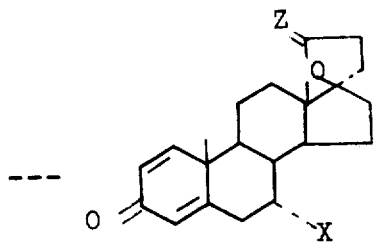   I        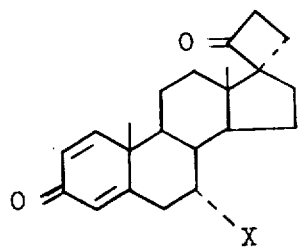   II ---.

UNITED STATES PATENT OFFICE
CERTIFICATE OF CORRECTION

Patent No. 4,079,054     Dated March 14, 1978

Inventor(s) Michael J. Green et al

It is certified that error appears in the above-identified patent and that said Letters Patent are hereby corrected as shown below:

Column 2, line 8, "-7α-chloro-17β-1,4-" should read ---7α-chloro-17α-1,4---; line 12, "-7α-iodo-17β-1,4-" should read ---7α-iodo-17α-1,4---; line 14, "-7α-halogen-" should read ---7α-halogeno---
Column 4, line 47, "(e.g. 3-oxo-16α-" should read ---(e.g. 3-oxo-17α---; line 64, "Additively," should read ---Alternatively,---.

Signed and Sealed this

Twenty-eighth Day of November 1978

[SEAL]

Attest:

RUTH C. MASON
Attesting Officer

DONALD W. BANNER
Commissioner of Patents and Trademarks